United States Patent [19]
Han et al.

[11] Patent Number: 6,117,903
[45] Date of Patent: *Sep. 12, 2000

[54] EXTRACTS OF SALVIA SPECIES HAVING ANTIVIRAL ACTIVITY

[75] Inventors: Myun K. Han, Silver Spring; Paul Lee, Phoenix, both of Md.

[73] Assignee: Georgetown University, Washington, D.C.

[*] Notice: This patent is subject to a terminal disclaimer.

[21] Appl. No.: 09/377,038

[22] Filed: Aug. 19, 1999

Related U.S. Application Data

[63] Continuation of application No. 08/985,105, Dec. 4, 1997, Pat. No. 5,994,400.
[60] Provisional application No. 60/032,618, Dec. 5, 1996.

[51] Int. Cl.$^7$ ............................. A01N 65/00; A01N 37/10
[52] U.S. Cl. .......................................... 514/533; 424/195.1
[58] Field of Search .......................... 424/195.1; 514/533

[56] References Cited

U.S. PATENT DOCUMENTS

| | | | |
|---|---|---|---|
| 5,994,400 | 11/1999 | Han et al. | 514/532 |
| 6,037,369 | 3/2000 | Han et al. | 514/532 |

*Primary Examiner*—Frederick Krass
*Attorney, Agent, or Firm*—Burns, Doane, Swecker & Mathis, L.L.P.

[57] ABSTRACT

This invention provides extracts of Salvia species essentially consisting of that fraction from a Salvia that precipitates from aqueous solution at pH $\leq 3$, said precipitate having the property such that it is is essentially fully dissolved in aqueous solution at pH 6, with solubility beginning to be readily observable at about pH 4, said extract having a molecular weight of $\leq 3500$ datons. A preferred embodiment of the invention provides active agents having a molecular weight of $\leq 1000$ daltons.

16 Claims, 2 Drawing Sheets

EXTRACTS OF SALVIA SPECIES HAVING ANTIVIRAL ACTIVITY

This application is a continuation, of application Ser. No. 08/985,105, filed Dec. 4, 1997 now U.S. Pat. No. 5,994,400; which takes priority from Provisional Application No. 60/032,618; filed Dec. 5, 1996.

FIELD OF THE INVENTION

This invention is related to the use of extracts of the genus Salvia, plants found in the Far East, to inhibit viral replication.

BACKGROUND OF THE INVENTION

The *Salvia miltiorrhiza* (SM) has long been used in traditional Chinese medicine for treatment of cardiovascular and hepatic diseases. These plants have several components which can be extracted. Components of the root have been extracted initially with 95% ethanol followed by extraction with cold water or with hot water. Both fractions extracted in water have shown antiviral activity and have shown minimal toxicity in animals.

Retroviruses possess the ability to reverse the normal flow of genetic information from genomic DNA to mRNA. The emergence of human immunodeficiency virus type (HIV) as an important human pathogen has led to a resurgence of scientific interest in retroviruses. In particular, scientific evidence indicates that the simple life cycle delineated above is not a completely accurate description of the replication cycle of all the members of this viral genus. For example, HIV-1 encodes no fewer than six gene products in addition to the characteristic retroviral Gag, Pol, and Env, and these are translated from a novel set of singly spliced and multiply spliced viral mRNA species. At least two of these additional proteins, termed Tat and Rev, act in trans to directly regulate HIV-1 gene expression. Therefore, the steps between penetration and proviral integration appeared quite similar for both MLV (murine leukemia virus) and HIV-1, although post-integration events were found to be significantly more complex in the latter. More recently, it has become evident that HIV-1 is merely one of a whole class of animal retroviruses that are now referred to as complex retroviruses. Retroviruses belonging to this complex retroviruses included all lentiviruses, spumaviruses, as well as HTLV-1 and related viruses (Table 1).

TABLE 1

Major taxonomic divisions among retroviruses

| Category | Subgroup | Prototype | Other examples |
|---|---|---|---|
| Simple retroviruses | C-type retroviruses group A | RSV | ALV, ASV |
|  | C-type retroviruses group B | MLV | FeLV, MSV, SNV, REV, SSV |
|  | B-type retroviruses | MNTV |  |
|  | D-type retroviruses | MPMV | SRV-1 |
| Complex retroviruses | Lentiviruses | HIV-1 | HIV-2, SIV, visna virus, FIV, |
|  | T-cell leukemia viruses Spumaviruses | HTLV-1 | EIAV HTLV-11, STLV, BLV |
|  |  | HSRV | SFV, BFV |

Abbreviationas: RSV, Rous sarcoma virus; ALV, avian leukemia virus; ASV, avian sarcoma virus; FeLV, feline leukemia virus; MSV, murine sarcoma virus; SNV, spleen necrosis virus; REV, reticuloendotheliosis virus; SSV, simian sarcoma virus; MMTV, mouse mammary tumor virus; MPMV, Mason-Pfizer monkey virus; SRV-1, simian retrovirus type simian T-cell leukemia virus; BFV, bovine foamy virus Although retroviruses are from a clearly defined and relatively homogeneous viral genus, they have been historically subdivided into three taxonomic groupings, primarily on the basis of the pathologic consequences of infection. The oncovirus subgroup includes retroviruses that have the ability to cause neoplastic disease in the infected host as well as several related, yet apparently benign viruses. Lentiviruses cause slow, chronic diseases that generally, although not always, lack a neoplastic component. Members of the spumavirus subgroup cause a marked foamy cytopathic effect in tissue culture. They have yet to be clearly associated with any human or animal disease.

Retroviral replication initiates with the intracytoplasmic penetration of the virion core, a process mediated by the specific interaction of the viral envelope glycoprotein with a specific cell surface receptor. Subsequently, a virion-associated RNA-dependent DNA polymerase transcribes the single-stranded RNA genome into a double-stranded linear DNA proviral intermediate (reverse transcription). Integration protein (integrase) specifically recognizes both ends of the viral DNA and removes two nucleotides from the 3'-ends (3'-donor processing). The processed viral DNA and integrase then migrate to the nucleus, where a viral integrase covalently links the retroviral genome to host chromosomal DNA (strand transfer), thereby forming the retroviral provirus.

The importance of HIV-1 as a human pathogen has led to its being the major focus of research into lentivirus replication and gene regulation. Indeed, HIV-1 may be viewed as the prototype of not only the lentivirus subgroup but also, more broadly, complex retroviruses in general.

With respect to the development of anti-viral drugs, there are numerous attractive targets to inhibit the retrovirus life cycle (reverse transcriptase, protease, and integrase). To date, of the numerous compounds that have already been identified and approved for marketing by the FDA for HIV only reverse transcriptase and protease inhibitors have been identified.

Recent studies have demonstrated that combinatorial therapy against reverse transcriptase (RT) and protease can eliminate a majority of the HIV viruses in T lymphocytes. Unfortunately, the small fraction of remaining viruses mutate and continue to replicate even in the presence of these drugs. High rates of replication, viral sequence mutation, and rapid turnover of the viral population are typical traits of retroviruses. These traits are even more striking in the case of HIV-1.

Despite the significant progress that has been made in studying the molecular mechanisms of HIV, current anti-HIV chemotherapies have many shortcomings including toxic effects and the induction of resistant strains of virus after relatively short treatment periods. As result, these drugs lack needed long term benefits necessary for complete treatment or prevention of HIV-infection.

Currently used inhibitors of reverse transcriptase and protease, chemically complex molecules, are enormously expensive. Current estimates indicate that the typical HIV-1 positive patient will spend anywhere from $12,000–$20,000 per year. The 90% of people infected with HIV reside in the developing world, therefore, and even a majority of those in industrialized countries, could not possibly have access to these agents. Therefore, it is apparent that more economically feasible approaches must be sought.

SUMMARY OF THE INVENTION

The instant invention provides extracts of genus Salvia having antiviral activity as an alternative to the presently known and used viral inhibitors. The invention provides extracts of Salvia species essentially consisting of that fraction from a Salvia that precipitates from aqueous solution at pH $\leq 3$, said precipitate having the property such that it is is essentially fully dissolved in aqueous solution at pH 6, with solubility beginning to be readily observable at about pH 4, said extract having a molecular weight of $\leq 3500$ datons. A preferred embodiment of the invention provides active agents having a molecular weight of $\leq 1000$ daltons. This disclosure also provides the first report that water-soluble extracts of Salvia yunnanenesis are useful for treatment of retroviral infections. The invention is exemplified herein using extracts of Salvia miltiorrhiza (SM) and Salvia yunnanensis (SY). The active isolates precipitate from the Salvia species under aqueous conditions at a pH of $\leq 3$. The precipitate begins to solubilize at pH of about 4, with complete solubility existing at pH $\geq 6$ and the pI is about 6.5. The most active component has molecular size of $\leq 1000$ daltons as determined by dialysis and by electrospray ionization mass spectrometry. The mass spectra data determined components to have atomic mass units of approximately the following: 79.8, 110.0, 136.1, 180.1 198.4, 296.2, 494.3 and 984.1. The agents of the invention may be administered in pharmaceutically acceptable carriers systemically or locally.

DETAILED DESCRIPTION OF THE INVENTION

Figure 1:
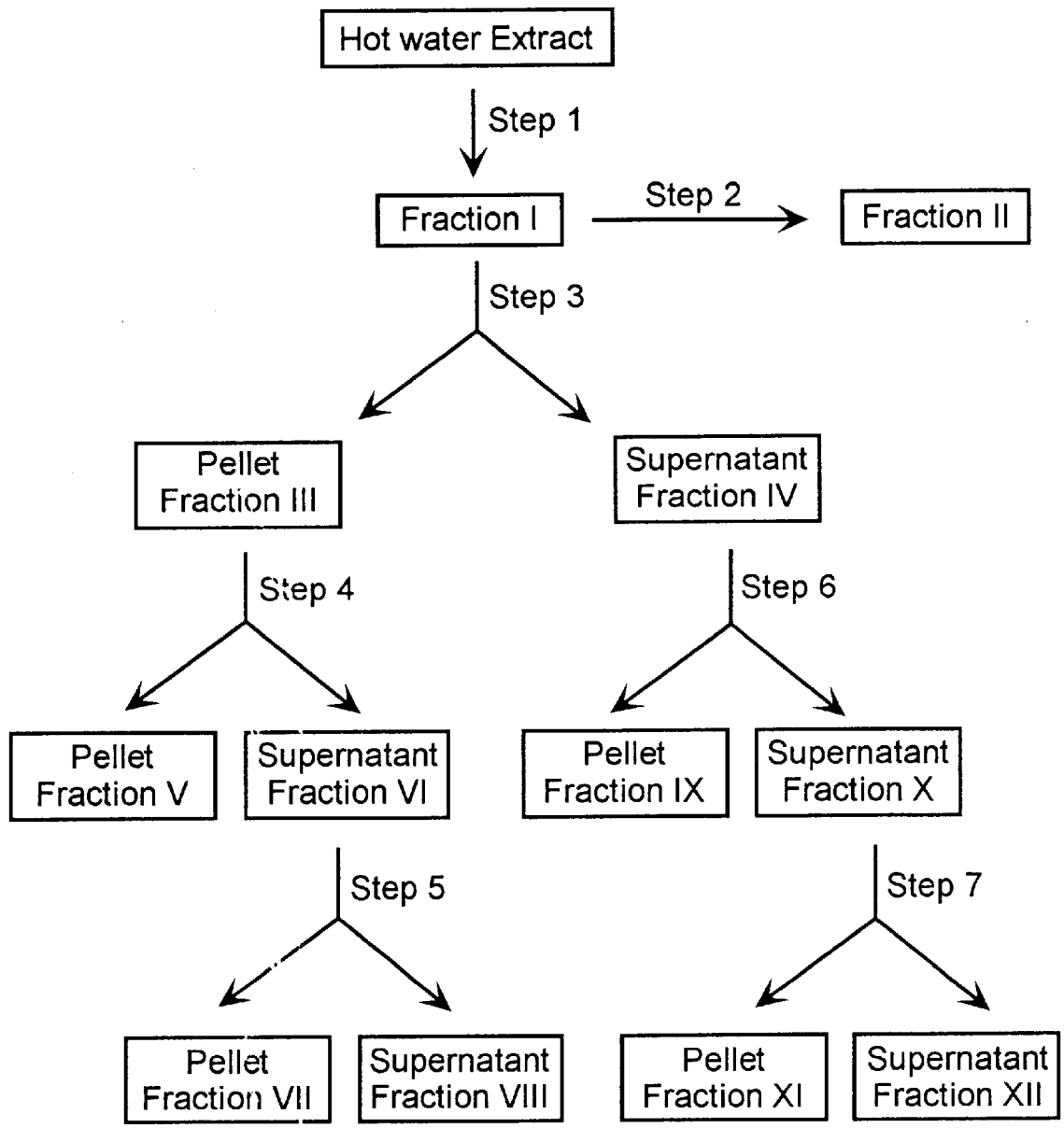
FIG. 1 is a flowchart showing steps of purification using acid precipitation followed by dissolving the precipitate in base.
Figure 2:
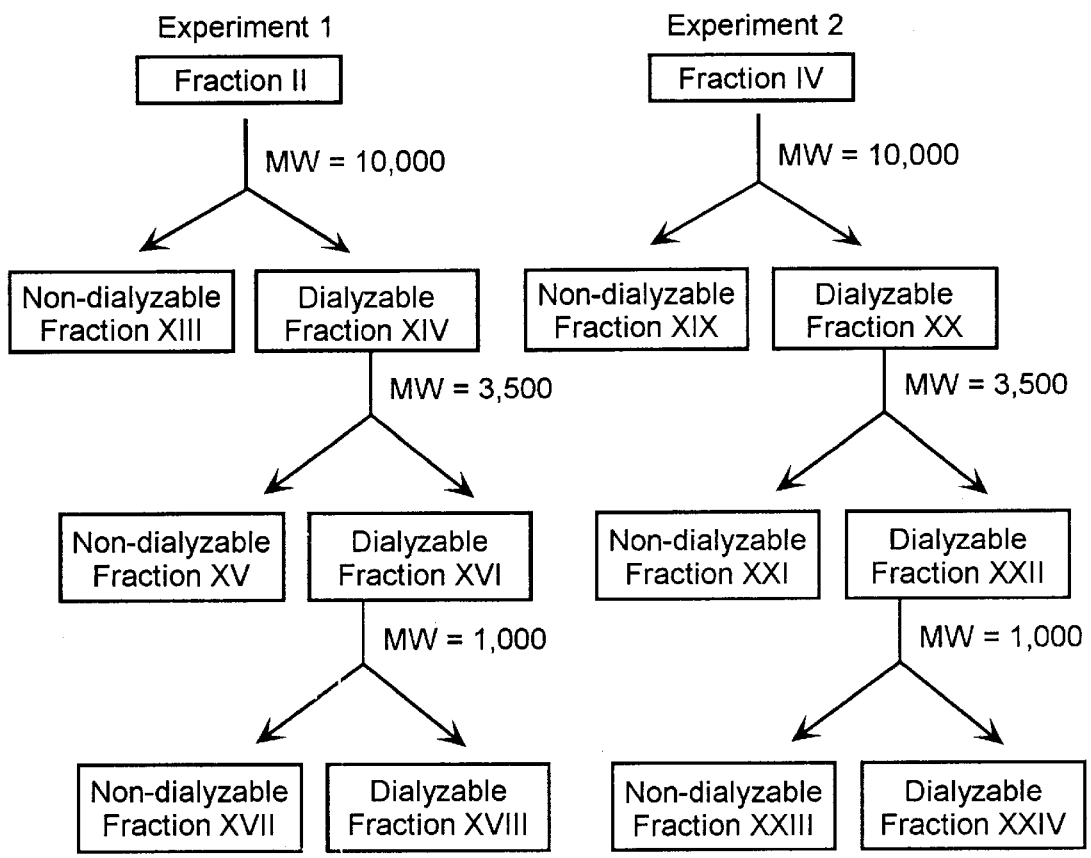
FIG. 2 is a flowchart showing steps for isolation of fraction of decreasing molecular weight by means of dialysis using membrane so varying porosity.

This invention uses an approach to prepare drugs that are derived from plant extracts. These active agents inhibit retroviral integration and replication, essential steps in the retrovirus lifecycle. The steps involved in proviral integration appear quite similar for both simple and complex retroviruses. There are significant similarities found in structural and functional properties among all types or classes of retroviral integrases and reverse transcriptase (RT) studied to date. Because of this commonality of mechanism, an inhibitor of polymerase, viral integrase and/or RT will inhibit a wide range of organisms such as human immunodeficiency virus (HIV), simian immunodeficiency virus (SIV), Feline Immunodeficiency Virus (FIV), Feline Leukemia Virus (FeLV), Murine leukemia virus (MuLV), Rous Sarcoma Virus (RSV), Bovine Immunodeficiency Virus (BIV), Human T-Cell Leukemia virus (HTLV). The active agents of the invention may also be used as inhibitors of other viral replication proteins such as reverse transcriptase, polymerase and integrase-like proteins. In addition to these retroviruses, the active agents of the invention may be used as inhibitors against organisms which produce vital polymerase and large T-antigen (a protein involved in the integration of viral DNA into host chromosomes) proteins such as the causative agents of hepatitis (including hepatitis B virus (HBV)) and human papillomavirus.

Preparation of Extracts From SM and SY Extracts

Plant extracts of S.M. and S.Y were made. The various fractions of plant extracts were obtained by the following procedure (See Flowchart 1).

The selected plant roots were initially washed with water to remove residual debris remaining from the harvesting of the plant. The roots were dried, then cut into small pieces. To the dried pieces of root, a 10 fold excess (v:v) of Mili-Q $dH_2O$ (18 mOhm/cm) was added and the roots were boiled at 98–100° C. for 4 hours. The mixture was then filtered through a 50 $\mu M$ filter. The filtered extract was then concentrated at 50° C. and 720 mmHg to a final density of 1.3 g/ml. The final yield was approximately 34% of the total weight of the ground root.

Step 1: The extract was diluted 1:5 with $dH_2O$, centrifuged at 8,000 rpm for 90 min at 25° C. in a GS-3 rotor. The pellet was discarded and the supernatant was saved. To this supernatant a one tenth volume of 1.0 N HCl solution is added to make a final concentration of 0.1 N HCl. This product was incubated overnight at 25° C. The solution is centrifuged at 8,000 rpm for 90 min at 25° C. in a GS-3 rotor and the resulting pellet was then washed with 95% ethanol followed by filtration through a 0.2 $\mu m$ filter system. This was repeated until the wash solution becomes clear. The pellet was then dried in the filtration unit at room temperature followed by incubation at 70° C. oven overnight. The powder was resuspended in $dH_2O$ at a 1:5 (w/w) ratio of pellet to water. The resulting product was then centrifuged at 25,000 rpm for 30 min at 25° C. in a Ti45 rotor; the supernatant was discarded and the resulting pellet washed with 95% ethanol by filtration using 0.2 $\mu m$ filter system and dried as described above. The powder was designated Fraction I. The yield of this pellet was approximately 0.5% of the total ground root.

Step 2: Fraction 1 was resuspended in 3% $NH_4OH$ solution and centrifuged at 25,000 rpm for 30 min at 25° C. in the Ti45 rotor. The supernatant was saved and 100% ethanol added to make a final ethanol concentration of 75%. After an overnight incubation at 25° C., the solution was centrifuged at 25,000 rpm for 30 min at 25° C. in a Ti45 rotor. The supernatant solution was discarded and the pellet is washed with 95% ethanol, filtered, and dried as described in above. This dried pellet is designated Fraction II.

Step 3: Fraction I was washed with 77% ethanol until the supernatant solution became clear. The supernatant solution was filtered using 0.2 $\mu m$ filter system (designated Fraction IV). The insoluble pellet was dried by an overnight incubation at 70° C. This dried powder was designated Fraction III.

Step 4: Fraction III was incubated with $dH_2O$ overnight with stirring at 25° C. The solution was then centrifuged at 25,000 rpm for 30 min at 25° C. in the Ti45 rotor. The pellet was dried by incubating over night at 70° C., The dried powder was designated Fraction V. The supernatant solution was designated Fraction VI.

Step 5: Fraction VI was treated with a one tenth volume of 1.0 N HCl solution to make a final concentration of 0.1

N HCl. The sample was incubated over night at 25° C., then centrifuged at 25,000 rpm for 30 min at 25° C. in the Ti45 rotor. The dried pellet was designated Fraction VII. The supernatant solution is designated Fraction VIII.

Step 6: Fraction IV was concentrated ten fold through a rotor-vap. The removal of ethanol and the concentrating of the sample resulted in partial precipitation of the extract due to a lowering of the pH to below 3, with precipitation being essentially complete at pH 2. The mixture was diluted 1:5 with water (v/v) and then centrifuged at 25,000 rpm for 30 min at 25° C. in the Ti45 rotor. The dried pellet and the supernatant solution were designated Fraction IX and Fraction X, respectively.

Step 7: Fraction X was treated with a one tenth volume of 1.0 N HCl solution to make a final concentration of 0.1 N HCl, then incubated overnight at 25° C. The solution was then centrifuged at 8,000 rpm for 90 min at 25° C. in a GS-3 rotor. The resulting dried pellet and the supernatant solution were designated Fraction XI and Fraction XII, respectively.
Physical and Chemical Properties of Various S.M. and S.Y. Fractions
1. Determination of pH-Dependent Solubility The acid induced precipitate contained the majority of the active anti-viral components as summarized in Table I. During fractionation of the extracts, differential solubility characteristics were observed depending on pH treatment. To precisely assess the pH-dependent solubility characteristics of the fractions, the following series of studies were performed.

EXAMPLE 1

Nine hundred microliter samples of Fraction VI (3.6 mg/ml) were placed in each of 15 Eppendorf tubes to which a 100 μl of the appropriate concentrations of HCl and NaOH were added to make solutions with a final pH of 1 to 7. The solutions were mixed and centrifuged at 14,000 rpm at 4° C. for 30 min in a microcentrifuge. The supernatant solution was removed from each tube. The soluble fraction from each pH concentration was diluted 1:10. From tha, a 150 μl aliquot was diluted by the addition of 850 μl of 50 mM $NH_4OH$. The insoluble fractions were dissolved in 1 ml of 50 mM $NH_4OH$, which were then diluted by adding 850 μl of 50 mM $NH_4OH$ to each fraction of 150 μl. An absorption scan from 200 to 500 nm was performed on 1 ml of each pH soluble or insoluble fraction. The peak absorbance at 280 nm for each solution was measured. The results demonstrated that Fraction VI contains products that begin to precipitate at about at pH 4 and has completely precipitated at pH 2 or below (at pH 2.75, 50% of the sought product precipitates out of solution).

EXAMPLE 2

To assess the effect of ethanol on solubility, the study was repeated with and without 25% ethanol in a series of solutions having pH of from 1 to 14. As stated above, the pH solutions were centrifuged, the supernatant solution was removed, serially diluted, and an absorption scan from 200 to 500 nm was performed on each soluble fraction. The peak absorbance at 280 nm for each solution was determined. The results demonstrate that ethanol increases the solubility of the sought product by two fold, (found to be a very active agent, hereafter referred to as "AA") in pH solutions less than 3. In the presence of 25% ethanol, the plant extract displays high solubility across all pH ranges.

EXAMPLE 3

To assess the pH-dependent differential solubility between Fraction VI, Fraction VII, and Fraction VIII, an equal amount of each fraction was dried down and weighed out into 7 Eppendorf tubes. To these tubes, 0.2 M phosphate-citrate and phosphate buffered solutions from pH 2.2 to 8.0 were added. The solutions were mixed for 5 minutes, then centrifuged at 14,000 rpm at 4° C. for 30 min. The supernatant solution was removed, serially diluted 1.5 to 1000 in the same pH buffered solutions, and the absorbance scanned from 200 to 500 nm. Fractions were shown to have pH-dependent solubility as a function of absorbance at 280 nm versus pH in complete pH-dependent absorbance scans of the fractions. The results demonstrated that the fractions possess different pH-dependent soluble components. Fraction VI begins to become soluble at pH 3, is about 50% soluble at pH 5 and is completely soluble at pH 6. Fraction VII is insoluble below pH 5.0, but completely soluble at pH 7. Fraction VIII remains soluble between pH 2.0 and 8.0.
Assessment of Apparent Molecular Weight(s) Component(s) of Active Fractions
a) Dialysis As summarized in flowchart 2, two fractions, Fraction II and Fraction IV, are dialyzed against three different dialysis membranes having different molecular cutoffs: 10,000, 3,500, and 1,000.

EXAMPLE 4

Fraction II, dissolved in 0.1% $NH_4OH$ solution (v/v), was placed in 10,000 molecular weight cutoff membrane and dialyzed over night against 2 liters of 0.1% $NH_4OH$ solution. The solution that remained in the dialysis bag was designated Fraction XIII and the dialyzed solution was designated Fraction XIV.

Fraction XIV was concentrated to 100 ml via rotor-vap and placed in 3,500 molecular weight cutoff membrane. This fraction was dialyzed over night against 2 liters of 0.1% $NH_4OH$ (v/v) solution. The solution that remained in the dialysis bag was designated Fraction XV and the solution which dialyzed out of the bag was designated Fraction XVI.

Fraction XVI was concentrated to 100 ml via rotor-vap and placed in 1,000 molecular weight cutoff membrane. This fraction was dialyzed over night against 2 liters of 0.1% $NH_4OH$ (v/v) solution. The resulting non-dialyzable and dialyzable solutions were designated Fraction XVII and Fraction XVIII, respectively.

EXAMPLE 5

Fraction IV, dissolved in 77% ethanol solution (v/v), was dialyzed over night against 6 liters of 77% ethanol solution (v/v). As described in the FLOWCHART 2 and Experiment 1, Fractions XIX, XXI, and XXIII are non-dialyzable against 10,000, 3,500, and 1,000 molecular weight cutoff membranes, respectively. Fractions XX, XXII, and XXIV are dialyzable against 10,000, 3,500, and 1,000 molecular weight cutoff membranes, respectively.

The results of in vitro HIV-1 integrase assay of the above fractions are summarized in Table 2 (See below).
Electrospray Ionization Mass Spectrometry The 1,000 molecular weight dialyzable fraction and the 3,500 molecular weight dialyzable/1,000 molecular weight non-dialyzable fractions were both analyzed by positive and negative electrospray ionization mass spectrometry. The following atomic mass unit weights were common for both fractions: 79.8±5, 110.1±5, 136.1±5, 180.1±5, 198.4±5, 296.2±5, 494.3±5, and 984.1±5.
C. Biological Properties of S.M. and S.Y. Extracts It is a purpose of this invention to provide a means of purifying the active component(s) of the water-soluble extracts of plants of Salvia genus to obtain those fractions that inhibit integrase activity and act as anti-viral agents. Two requirements for an anti-viral are efficacy and safety at low concentrations of the drug. The following sections demonstrate efficacy and safety of Fraction I.

1. Efficacy of Viral Inhibition

In vitro HIV-1 Integrase Assay: In vitro assays to monitor the activity of HIV-1 integrase have been developed as described below. These assays utilize purified recombinant HIV-1 integrase and oligonucleotide substrates which correspond to the LTR ends of the viral DNA. These assays reflect the actual functional events which occur in vivo. Both fluorometric (Lee et al. (1995) *Analytical Biochemistry* 227, 295–301) and radioactive assays improve upon the previously published in vitro assay (Lee et al., (1995) Biochemistry 34, 10205–10214; Lee et al., (1995) Biochemistry 34, 10215–10223). Modification in methods of the enzyme preparation have improved the functional properties of the HIV-1 integrase sample (Lee and Han (1996) Biochemistry 35, 3837–3844; Lee et al. (1997) Biochemistry). These modifications in the assay and sample preparation provide for in vitro assays that better reflect the events which occur in vivo. Hence, results from the in vitro assay are very useful predictors of viral infectivity when searching for potential inhibitors against integrase.

In evaluating the activity of the various extract fractions in inhibiting HIV-1 integrase activity, the extract fractions were first dissolved in the appropriate volume of 0.1% $NH_4OH$ (w/v) to make the final concentration 15 mg of each fraction per ml. These samples were then centrifuged at 10,000 rpm for 30 min. If a pellet was formed the supernatant was removed, the supernatant was dried down and then redissolved in 0.1% $NH_4OH$. The resulting solutions were the stock solution of the extract fractions. From these stocks, the following dilutions were made: 1:10, 1:50, 1:100, 1:200, 1:300, 1:400, 1:500, 1:600, 1:700, 1:800, 1:900, 1:1000, 1:2000, 1:3000, 1:4000, 1:5000, and 1:10,000. 1 µl of each of these dilutions were added to each reaction mixture (total volume 20 µl) which corresponded a final concentration of 75, 15, 7.5, 3.75, 2.5, 1.875, 1.5, 1.25, 1.07, 0.9375, 0.833, 0.75, 0.375, 0.25 0.1875, 0.15, 0.075 µg/ml, respectively. Testing was then carried out as previously described (Lee et al., (1995) Biochemistry 34, 10205–10214; Lee et al., (1995) Biochemistry 34, 10215–10223; Lee and Han (1996) Biochemistry 35, 3837–3844).

To determine the IC 50 and IC 90 of each fraction, the gel was exposed to phosphorimager screening and the percent cleavage determined by the Molecular Dynamics Phosphorimager. The % inhibition was determined by subtracting % cleavage of each fraction from the % cleavage of the positive control and dividing this value by the % cleavage of the positive control. These values were then plotted as a function of concentration and the IC50 and IC 90 determined. The activities of Fraction I (starting material), Fraction XVII (dialysis) and Fraction VIII (Supernatant from the acid precipitation) were compared. Fraction VIII had very little activity while Fraction XVII showed improvement of the overall activity over the starting material (Fraction I). The IC 50's and IC 90's from all other fractions are summarized in the tables below:

TABLE 2

Inhibitory activity of various SY & SM fractions from FLOWCHART 1 against HIV-1 integrase activity in vitro.

| | $IC_{50}$ (µg/ml) | $IC_{90}$ (µg/ml) |
|---|---|---|
| SM Fractions | | |
| I | 2.8 | 3.5 |
| III | 2.1 | 4.0 |
| SY Fractions | | |
| I | 1.2 | 2.5 |
| II | 1.2 | 2.5 |
| III | 1.9 | 2.5 |
| IV | 1.9 | 2.5 |
| V | 1.9 | 2.8 |
| VI | 1.8 | 5.0 |
| VII | 1.2 | 2.5 |
| VIII | 8.0 | 15.0 |
| IX | 2.5 | 7.0 |
| X | N.D. | N.D. |
| XI | 0.9 | 3.5 |
| XII | 4.0 | 8.0 |

TABLE 3

Inhibitory activity of various SY fractions from FLOWCHART 2 against HIV-1 integrase activity in vitro.

| Fractions | $IC_{50}$ (µg/ml) | $IC_{90}$ (µg/ml) |
|---|---|---|
| XIII | 1.9 | 4.0 |
| XIV | | |
| XV | 1.4 | 3.1 |
| XVI | | |
| XVII | 0.85 | 1.6 |
| XVIII | 2.2 | 5.0 |
| XIX | | |
| XX | | |
| XXI | 2.4 | 4.0 |
| XXII | 2.4 | 7.0 |
| XXIII | 1.5 | 4.0 |
| XXIV | 1.5 | 4.0 |

These data indicate that the fractions which show the greatest inhibition are those precipitates obtained from the acid precipitation process. Repeated acid precipitation followed by base solubilization and dialysis improves the anti-integrase activity in the fractions because that process continues to remove the inactive compounds. The supernatant for the low pH solution from which precipitate has formed shows minimal activity. In addition, dialysis with membranes that have a molecular weight cutoff of 1000 shows that both the dialyzable and non-dialyzable fractions from the acid precipitates have activity.

Although it might be expected that the non-dialyzable fraction would not have molecules that are smaller than one thousand daltons, mass spectrometry of this fraction showed that this fraction contains molecules which are smaller than 1000 daltons. An explanation for this may be that the dialysis was performed in 77% ethanol, which reduces the size of the pores, making the dialysis a time-dependent process. However, this does not preclude one from saying that the most inhibitory molecules are smaller than 1000 daltons, since the dialyzable fractions also have inhibitory activity.

b.) In Vitro Reverse Transcriptase Assay

The same dilutions of Fraction VII from the in vitro integrase assay were used to determine the efficacy against Moloney murine leukemia virus (MMLV) RNaseH' reverse transcriptase (Gibco BRL). This assay is based on the synthesis of poly dT-DNA from a poly rA-RNA template by reverse transcriptase and incorporation of ($^3$H)dTTP in the formation of RNA/DNA hybrid duplex. The procedure is described in the publication edited by Aldovini and Walker (*Techniques in HIV Research* (1990) at page 98.) Using 10 units of reverse transcriptase per 50 μl reaction, the amount of ($^3$H)dTTP incorporated and bound to glass filters was quantified. The dilutions of Fraction VII were assayed in triplicate and demonstrated an IC90 and IC50 of 28 and 1.7 μg/ml, respectively. The IC50 for MMLV reverse transcriptase is comparable to that of HIV-1 integrase, but the IC90 is approximately 10 fold greater. These results indicate that the active components of Fraction VII contain anti-reverse transcriptase activity, although that fraction is not as effective at inhibiting reverse transcriptase as it is at inhibiting integrase. In addition, HIV-1 RT (Boehringer Mannheim) was assayed by the reverse transcriptase assay. This assay demonstrated an IC 90 and an IC 50 of 52 μg/ml and 12 μg/ml, respectively.

c.) In Vivo FIV Model

The Feline Immunodeficiency Virus (FIV) model is an accepted animal model for studying drugs for use against HIV infection. FIV is a T cell-trophic lentivirus isolated from felines. FIV resembles HIV biologically and biochemically, with high homology between FIV and HIV integrase. FIV infected cats develop Feline Acquired Immunodeficiency Syndrome (FAIDS) which is similar to full-blown AIDS in humans.

FIV model in cells In Vitro: The Crandell-Reese Feline Kidney (CrFK) cell line is susceptible to FIV infection and supports viral replication. CrFK cells are an efficient means for producing virus and assaying for FIV infection. Although FIV is not cytopathic for FIV infected CrFK cells, diagnostic assays are available for screening for FIV infection in tissue culture. Studies have demonstrated the efficacy of S.Y. Fraction I to prevent FIV infection.

Determination of ED90 and ED50: S.Y. Fraction I protects CrFK cells from FIV infection. CrFK cells were plated at a density of 1×10$^5$ cells/T25 flask in triplicate. Following a 24 hr incubation for cell attachment and growth, solutions of Fraction I were applied to the cell cultures for 24 hr. The solutions were made by dissolving Fraction I in dH$_2$O at a concentration of 100 mg/ml. The samples were then centrifuged at 25,000 rpm for 30 min at 25° C. in a Ti45 rotor. The supernatant solution was removed and three 1 ml aliquots are dried down by centrifugation under an open vacuum to determine the concentration of the solution. Fraction I was further diluted down to 2 mg/ml in dH$_2$O or DMEM, filtered through a 0.2 μm acetate cellulose filter, and the concentration determined by determining the mass of the dried solute compared to the tared control. Individual concentrations of Fraction I were made up in DMEM with 10% Fetal Bovine Serum and added to the cell cultures.

Following 24 hr incubation of cells in the presence of Fraction I, culture fluid from CrFK cells infected with FIV-AZR-1 (AZT resistant strain) was assayed for relative titre of FIV by a FIV p26 capture assay (IDEXX systems, Inc. FIV PET CHEK). FIV was diluted to an absorbance at 630 nm to a value of 0.2. One milliliter of FIV was applied to the cultures for 1 hour, followed by removal of the viral supernate and reapplication of the various concentrations of Fraction I. The cell culture media was changed at day 3 with the varying concentrations of Fraction I. At the end of six days, 0.2 ml of cell culture media was assayed for the presence of FIV by the FIV p26 capture assay. The FIV p26-capture assay uses two different monoclonal antibodies against FIV, one which is immobilized to the wells of a 96-well plate that captures FIV and another monoclonal antibody which is conjugated with horseradish peroxidase (HRPO). The anti-FIV p26-HRPO monoclonal antibody in the presence of substrate (hydrogen peroxide and TMB, a chromogen) produces a color signal proportional to the amount of FIV p26 antigen present in the media. The color signal is read by a 96 well plate reader at an absorbance of 630 nm. Fraction I at concentrations as high as 100 μg/ml does not interfere with the FIV p26 capture assay.

In this test, Fraction I showed an $ED_{90}$ of 5.0 μg/ml and an ED50 of 2.5 μg/ml in preventing FIV infection of CrFK cells. This study demonstrates that Fraction I will be efficacious in preventing FIV infection.

Determination of Treatment Time-course: To assess the time requirements for treatment of cells exposed to FIV, the following two studies were performed. In the first study, cells were plated out at 1×10$^5$ cells/T25 for 24 hr. One group (−24 hr group) was treated with 50 μg/ml of Fraction I prior to FIV infection. After one hour, all groups were infected with FIV-AZR-1. Fraction I at 50 μg/ml was applied to groups at 1, 24, 36, 48, 60, and 72 hours following infection. One group was not treated with Fraction I. The media on all groups was changed on the third day following FIV infection, and the presence of FIV in the media was assayed seven days after infection.

Treatment of CrFK cells with Fraction I prior to infection, 1 hr after infection, and 24 hr after completely protected the cells from FIV infection. Treatment after 36 hr resulted in a small percentage of cells being infected, but the presence of Fraction I prevented the rest of the culture from being infected. This trend continued to be seen at the 48, 60, and 72 hour readings. After 72 hours, up to 50% of FIV was inhibited. These results demonstrate that application of Fraction I can both protect against and decrease the extent of FIV infection following initial exposure to the virus.

In the second study, CrFK cells were plated out as described above, but all cells except the no treatment control were treated with 50 μg/ml of Fraction I for 24 hr. Following 24 hr incubation of cells in the presence of Fraction I, the cells were infected for 1 hr with FIV-AZR-1, and then retreated with Fraction I. At 24, 48, and 72 hr following infection, normal media was applied to the cell cultures. Five days following infection, the cell culture media was assayed for FIV. Exposure of cells to Fraction I following FIV infection for as short as 24 hours protected the cells from infection. These results demonstrate that removal of Fraction I did not remove protection against FIV infection. Exposure of cells to Fraction I following FIV infection for as short as 24 hours protected the cells from infection. Hence, in this study a window for protection against infection was demonstrated to exist from prior to infection to 24 hours post-exposure. This result indicates that Fraction I acts as a retroviral inhibitor. Its therapeutic benefit arises because virus released from infected cells is being inhibited from infecting uninfected cells so that as infected cells die off, other cells are not infected. The propagation of infection is thereby interrupted and the viral load decreased.

c.) Cell Culture Toxicology

To assess Fraction I toxicity in cell culture the following two toxicity studies were performed. First, the toxicity of Fraction I was determined by percent cell death on a confluent CrFK cell culture. Second, the toxicity of Fraction I was determined by inhibition of CrFK cell growth.

Determination of $LD_{90}$ and $LD_{50}$: To determine the 90% and 50% lethal dose of Fraction I on confluent CrFK cells, 1×106 cells were plated per T25 flask. Following a 48 hour incubation, solutions of Fraction I at 1.6, 1.2, 1.0, 0.8, 0.4, 0.2, 0.1, and 0 mg/ml were made in DMEM with 10% FBS and applied to the respective triplicate cultures. After incubating the cells for 72 hours in the presence of Fraction I, the number of viable cells per group was determined by the Trypan Blue exclusion assay. CrFK cells were trypsinized and diluted 1:1 in 0.4% Trypan Blue. The number of cells was determined by counting cells on a hemocytometer, indicating $LD_{90}$ and $LD_{50}$ of Fraction I were 1.6 mg/ml and 0.8 mg/ml, respectively, in this assay. This gives a Therapeutic Index (LD50/ED50) range of 320.

Determination of $IC_{50}$: To determine the 90% and 50% growth inhibitory doses of Fraction I, CrFK cells were plated at $1 \times 10^5$ per T25 flask. After 24 hr, solutions of Fraction I at 0.8, 0.4, 0.3, 0.2, 0.15, 0.1, 0.08, 0.05, 0.04, 0.03, 0.02, and 0 mg/ml were made up in DMEM with 10% FBS and applied to the respective triplicate cultures. The media was changed at day 3 and day 6 and the number of viable cells per group was determined by Trypan Blue exclusion assay as described above. In this assay, a dose of 0.4 mg/ml inhibited growth of CrFK cells by 90% while a dose of 0.2 mg/ml inhibited growth by 50%.

d. In Vivo Toxicology

To evaluate acute toxicity of Fraction I in an in vivo model, 10 young female Balb/C mice were given 600 mg/Kg of Fraction I for 28 days by oral gavage. Eight of the 10 mice survived treatment without any signs of morbidity. Two 2 mice died from human technical error in delivering Fraction I to the mice by oral gavage as determined by necropsy.

The results from the studies demonstrate no signs of toxicity in the organs or blood. Organ samples from the 8 mice that survived the duration of the study were harvested and analyzed (Vet Research Inc.). No microscopic evidence of toxicity was found in sections of the brain, thyroid, trachea, thymus, pancreas, skeletal muscle, urinary bladder, cervix, lymph node, kidney, spleen, heart, lung, liver, adrenal, kidney, uterus, lymph nodes, squamous and glandular stomach, small and large intestine, esophagus, skin, ovary or fat. In addition, blood chemistry analyses were performed on blood samples of the mice following completion of the study. Table 4 shows that most of the blood components are in the normal range.

TABLE 4

Standard Blood Chemistry Values and Experimental Values.

| Test component | High-Low Values | Mean with Std. Dev. | Value |
|---|---|---|---|
| Glucose (mg/dl) | 124–250 | 185 ± 75 | Normal |
| Creatine (mg/dl) | 0.21–0.66 | 0.71 ± 0.21 | High |
| | 3.95–6.21 | 4.6 ± 0.44 | Normal |
| Albumin (g/dl) | 2.58–4.58 | 3.11 ± 0.23 | Normal |
| Total bilirubin (mg/dl) | 0.04–0.74 | 0.19 ± 0.09 | Normal |
| Calcium (mg/dl) | 8.2–12.6 | 8.8 ± 0.37 | Low Normal |
| Inorganicphosphorous (mg/dl) | 6.0–10.0 | 10.45 ± 7.3 | High |
| Alkaline phosphatase (IU/L) | 45–175 | 51.4 ± 32.5 | Low Normal |
| ALT (GPT) (IU/L) | 24–77 | 27.4 ± 10.0 | Low Normal |
| AST (GOT) (IU/L) | 53–269 | 162.8 ± 110.5 | Normal |
| Sodium (mEq/L) | 115–189 | 147.6 ± 3.7 | Normal |
| Potassium (mEq/L) | 5.1–10.4 | 7.8 ± 2.4 | Normal |
| Chloride (mEq/L) | 82–114 | 117 ± 5.3 | High |

Another larger study evaluated acute toxicity of Fraction I in the mouse model. It was designed to assess the potential risks/side effects of chronic long term exposure to greater than one log difference in concentration of Fraction I. The study consisted of the following 8 groups each of 12 Balb/C mice:

| Group | Sex | Treatment |
|---|---|---|
| 1 | Female | Water |
| 2 | Female | 500 mg/Kg |
| 3 | Female | 100 mg/Kg |
| 4 | Female | 25 mg/Kg |
| 5 | Male | Water |
| 6 | Male | 500 mg/Kg |
| 7 | Male | 100 mg/Kg |
| 8 | Male | 25 mg/Kg |

In a blind study, Fraction 1 at 500, 100, and 25 mg/Kg animal weight was administered every day for 28 days to 8 groups of 12 Balb/C mice by oral gavage with manual restraint. Every week blood samples from a subgroup (4 mice) were collected and pooled for blood chemistry. Following 28 days, the mice were anesthetized and exsanguinated by cardiac puncture. Individual mouse blood was collected for CBC's with differentials and SMAC24 biochemical serum analysis. Tissue samples were taken for histopathologic processing and evaluation. No evidence of toxicity was found upon analysis of the blood or tissue samples.

Compositions of the invention may be administered in pharmaceutically acceptable carriers. Compositions should be administered in sufficient dosage to obtain a blood concentration of 10 nM to 1000 nM containing as active agents molecules of ≦3500 daltons from the extracts. When the compositions contain larger molecules of the extracts, it is necessary to administer doses to obtain concentration of up to 10000 nM in the blood. In general, extracts of SY require about ⅕ the dosage of SM extracts. When using extracts of SY, blood concentration of as low a 1 nM may be sufficient.

Compositions of the invention may be administered orally, systemically or topically. Compositions for oral administration may by be administered in liquid form or as tablets or capsules. For parenteral administration, carriers such as saline, glucose, phosphate buffered saline, and the like may be used. For administration to the central nervous system, compositions may be administered into the cerebral spinal fluid. For intrathecal administration, carriers for parenteral administration, particularly carriers such as glucose in water or saline are appropriate. The compositions may also be prepared in liposomes to enhance transfer across membrane barriers. Of course, compositions for parenteral use, including compositions for intravenous, intramuscular, subcutaneous or intrathecal administration, will be provided in sterile solutions.

For topical application, the compositions may be administered on a solid support such as a gauze or sponge. For example, such solid supports may be inserted into the vagina or rectum to provide treatment. The active agents of the invention may also be applied to condoms to enhance protection against infection. Compositions may also be prepared in the form of lotions or salves for topical application. The active agents may, for example, be applied to the vagina or rectum in the form of suppositories, enemas or douches.

While the active agents of the invention encompass all fractions of the genus Salvia which precipitate from aqueous solution at pH of ≦3 and re-dissolve at pH 4–6, all water soluble extracts of *Salvia yunnanensis*, which have never previously been reported to have anti-retroviral activity, are encompassed within the invention, all of said extracts having been found, surprisingly, to have unexpectedly high activity.

Compositions may be administered intranasally as a mist. Compositions of the invention may also be administered topically in gel or lotion form.

The active fractions may also be lyophilized and vialed. The lyophilized material may then be solubilized to provide dosage forms. Additionally, the lyophilized material may simply be snorted for nasal administration.

The active agents of the invention may also be administered in beverage or food. As an example, the extracts may be placed in feed of cats to treat or prevent Feline leukemia virus.

What we claim is:

1. A composition of matter suitable for use as an antiviral agent that contains an antiviral effective amount of a composition that contains at least one anti-viral compound which compound is contained in a salvia extract produced by acidic precipitation at a pH of 4.0 or less; wherein said compound possesses a molecular weight of $\leq 3500$ daltons, and wherein said composition exhibits an $IC_{50}$ ($\mu$g/ml) against HIV-1 integrase in vitro of no more than 2.8 $\mu$g/ml.

2. The composition of claim 1 wherein said IC50 value is no more than 0.85 $\mu$g/ml.

3. The composition of claim 1 which is obtained by repeated acid precipitation followed by base solubilization and dialysis.

4. The composition of claim 1 which is suitable for pharmaceutical usage as an antiviral agent, and is administrable by a method selected from oral, systemic or topical.

5. The composition of claim 1 which is administrable by parenteral means.

6. The composition of claim 5 wherein parenteral means is selected from the group consisting of intravenous, intramuscular, subcutaneous, and intratrecal administration.

7. The composition of claim 1 wherein said compound possesses a molecular weight of $\leq 1000$ daltons.

8. The composition of claim 1 which is in the form of a tablet, capsule or sterile solute.

9. A method of treating a person having a viral infection comprising administering a therapeutically effective amount of a composition of matter according to claim 1.

10. A method of treating a person having a viral infection comprising administering a therapeutically effective amount of a composition of matter according to claim 2.

11. A method of treating a person having a viral infection comprising administering a therapeutically effective amount of a composition of matter according to claim 3.

12. A method of treating a person having a viral infection comprising administering a therapeutically effective amount of a composition of matter according to claim 4.

13. A method of treating a person having a viral infection comprising administering a therapeutically effective amount of a composition of matter according to claim 5.

14. A method of treating a person having a viral infection comprising administering a therapeutically effective amount of a composition of matter according to claim 6.

15. A method of treating a person having a viral infection comprising administering a therapeutically effective amount of a composition of matter according to claim 7.

16. A method of treating a person having a viral infection comprising administering a therapeutically effective amount of a composition of matter according to claim 8.

* * * * *